United States Patent [19]

Tribble et al.

[11] Patent Number: 4,961,419

[45] Date of Patent: Oct. 9, 1990

[54] MEN'S UNDERWARE WITH PENILE ENVELOPE

[76] Inventors: Alice K. Tribble; Joe L. Tribble, both of 721 Northwest 49th, Oklahoma City, Okla. 73118

[21] Appl. No.: 242,681

[22] Filed: Sep. 12, 1988

[51] Int. Cl.$^5$ .................................. A61F 5/40
[52] U.S. Cl. .................................. 128/159; 128/158; 2/403
[58] Field of Search ............... 128/158, 159, 160, 168; 2/2, 403, 401, 405

[56] References Cited

U.S. PATENT DOCUMENTS

| | | | |
|---|---|---|---|
| 2,601,602 | 6/1952 | Firsching, Sr. | 2/224 |
| 3,487,833 | 1/1970 | Senser | 128/159 |
| 4,345,337 | 8/1982 | Chung | 2/405 |
| 4,414,971 | 11/1983 | Chung | 128/159 |
| 4,440,817 | 4/1984 | Ahlm | 428/71 |
| 4,471,772 | 9/1984 | Miller, Jr. | 128/159 |
| 4,509,512 | 4/1985 | LeClercq | 128/160 |
| 4,526,167 | 7/1985 | Ebenal et al. | 128/158 |
| 4,622,962 | 11/1986 | Kauffman | 128/158 |
| 4,660,551 | 4/1987 | Nishimura | 128/79 |
| 4,702,239 | 10/1987 | Ichikawa | 128/159 |
| 4,759,355 | 7/1988 | Thrower | 128/159 |

FOREIGN PATENT DOCUMENTS 2258805  9/1975  France .................................. 2/405

Primary Examiner—Randall L. Green
Assistant Examiner—Paul Prebilic
Attorney, Agent, or Firm—Laney, Dougherty, Hessin & Beavers

[57] ABSTRACT

An underwear garment that is specially constructed to be worn by men having semi-rigid penile implants. The construction includes not only a general type of a brief but also an athletic model, each of which is adapted to include a specifice type of front panel interior pocket or envelope that is constructed of a plurality of panels of material with each panel contributing a particularly desirable retention function. The envelope consists of outer paneling which exerts significant inward retentive pressure against the body and penis while a next layer of soft, thick batting material provides cushioning thereby to avoid abrasive tendencies of the structure. Finally, the inner contacting panels which directly envelope the penis are formed of a very soft fabric having a smooth surface in actual contact with the organ. The alternative sports model necessitates a stronger waistband elastic which, in turn, requires that a soft fabric window portion be placed adjacent the upper portion of the penis member.

7 Claims, 2 Drawing Sheets

MEN'S UNDERWARE WITH PENILE ENVELOPE

1. Field of the Invention

The invention relates generally to men's undergarments and, more particularly, but not by way of limitation, it relates to specially constructed underwear for use by men having such as a penile prosthesis which renders the organ permanently erect or semi-erect.

2. Description of the Prior Art

The prior art includes numerous types of special purpose men's brief or undergarment that are especially directed to special padding or fabric construction in the crotch or penis area for the purpose of aiding in comfort and natural disposition. Early developments saw such special purpose briefs as being primarily concerned with positioning of the penis and/or scrotum in a generally downward attitude and with an aim toward sanitation and alleviation of hot, binding carriage during certain activities. Special purpose underwear has been devised for driving, surgical recuperation and other activities that may require accommodation in and around the genitalia.

More specifically, U.S. Pat. No. 4,471,772 teaches a male undergarment for strapping the flaccid penis in a relatively straight line for reasons of preserving fertility through proper circulation. U.S. Pat. No. 4,345,337 teaches a men's brief including a penile support member for the purpose of enabling free air circulation. U.S. Pat. No. 4,660,551 in the name of Nishimura teaches a complex strapping assembly for the front portion of a man's brief which again is intended for improving air circulation and avoiding heat rash and related problems. A U.S. Pat. No. 4,526,167 is more directly constructed for supporting the sex organ after major surgery, and the undergarment includes a front envelope panel into which the organ can be buttoned for safe keeping and proper positioning. U.S. Pat. No. 2,601,602 teaches a male undergarment that includes a forward compartment with access slit for deposition and safe keeping of the genitalia, both penis and scrotum. This device is especially designed for use when driving an automobile to provide proper ventilation and support in the sitting attitude. Finally, U.S. Pat. No. 4,509,512 teaches a bikini-type male undergarment which includes a forward pocket wherein the male organ may be placed and enclosed by means of VELCRO® enclosure. This undergarment is specifically designed for supporting the erect penis which results from such as a semi-rigid penile implant.

Summary of the Invention

The present invention relates to a male undergarment for comfortably restraining and retaining a male organ having a semi-rigid penile implant. The undergarment is structured to appear externally as close as possible to a usual brief-type underwear, e.g., of the jockey short type. Inner paneling of the brief includes a specific form of pocketing enclosure having an interior access slot and being covered with a soft, comforting material on the inside. The brief includes a relatively strong expansible fabric on the outside while having a thicker, felt-like cushioning material between the inner and outer plies. Such brief structure results in the circumferal retention about the upright rigid penis while also providing a very soft contacting surface in immediate surround of the penis. In an alternative design, a sports model, the structure uses stronger elastic banding, particularly around the waist and lower abdominal portions, with a window portion presenting soft, non-strictive pressure in the area of the penis head and glans.

Therefore, it is an object of the invention to provide an underwear for use by persons having penile implant prostheses which will best subdue any outward indications of irregularity.

It is also an object of the present invention to provide an undergarment for comfortably restraining a rigid penis.

It is still another object of the present invention to provide an undergarment that appears similar to regular men's briefs but has the penile restraining capability for the upright prosthetic penis.

Finally, it is an object of the present invention to provide restraining underwear for use by the person having a penile implant of the semi-rigid type which underwear is both comfortable and effective in masking outward indications of the rigid penis.

Other objects and advantages of the invention will be evident from the following detailed description when read in conjunction with the accompanying drawings which illustrate the invention.

Detailed Description of the Invention

Figure 1:
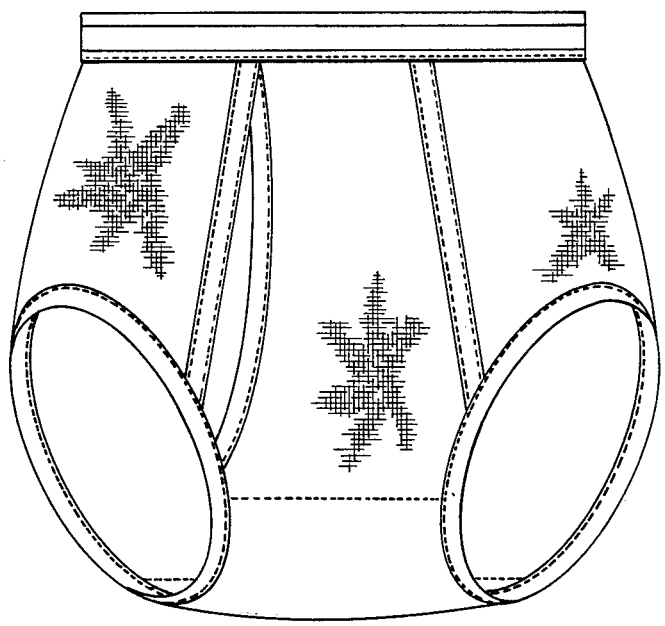
FIG. 1 is a front view in elevation of the men's briefs of the present invention.

FIG. 1 illustrates a pair of jockey-type men's briefs 10 which embody the present invention as sewn into the construction of the front paneling and crotch. In conventional manner, the briefs 10 include a waist strip 12 which consists of a band of relatively heavy elastic, i.e., a polyester rubber elastic material of selected weight and elasticity. The body 13 of the briefs may be constructed of Lycra SPANDEX ™ material of light weight that provides two-way stretch capability. The body 13 consists of SPANDEX ™ side panels 14 and 16 joined to rear panel 18 as sewn around the top to the waist band 12. The body 13 may be formed as a single panel overlapping in front or it may consist of plural segments joined together. A crotch panel 20 of SPANDEX ™ is sewn to the lower side of rear panel 18 to extend forwardly upward to waistband 12 while also providing the fly front panel 22. The fly front panel 22 is for cosmetic purposes only and is secured in front of retaining structure 24 as the entire front structure is secured in briefs 10 by right and left double-stitched tapes or seams 26 and 28, respectively. The leg openings 30 and 32 are each formed in conventional manner with a circular loop of polyester rubber elastic as covered by an inwardly seamed ribbed cotton material.

Figure 2:
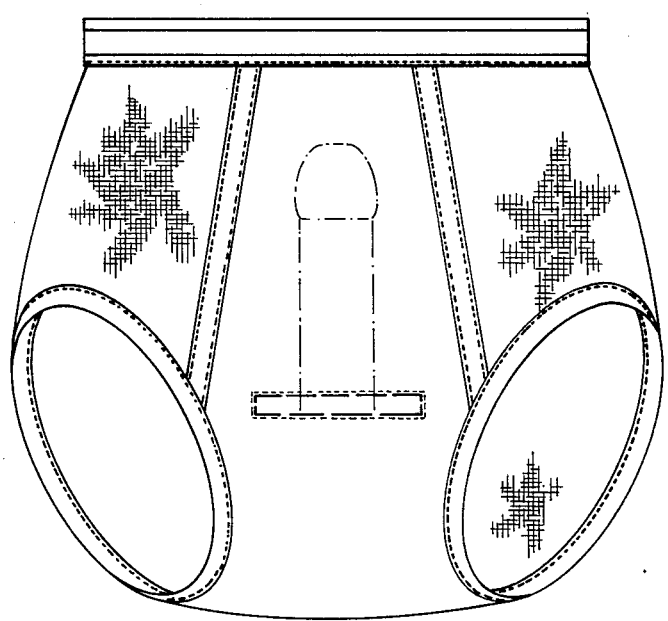
FIG. 2 is the front view of FIG. 1 with interior structure shown in phantom.

FIG. 2 illustrates the briefs 10 as shown with the wearer's penis 34 disposed in relative position and with the cosmetic fly front panel 22 removed. Thus, as the briefs are worn, the erected penis 34, as will result from certain prostheses, is inserted through an interior slit 36 to be secured rigidly upright behind the containment structure 24.

Figures 3, 4, 5:
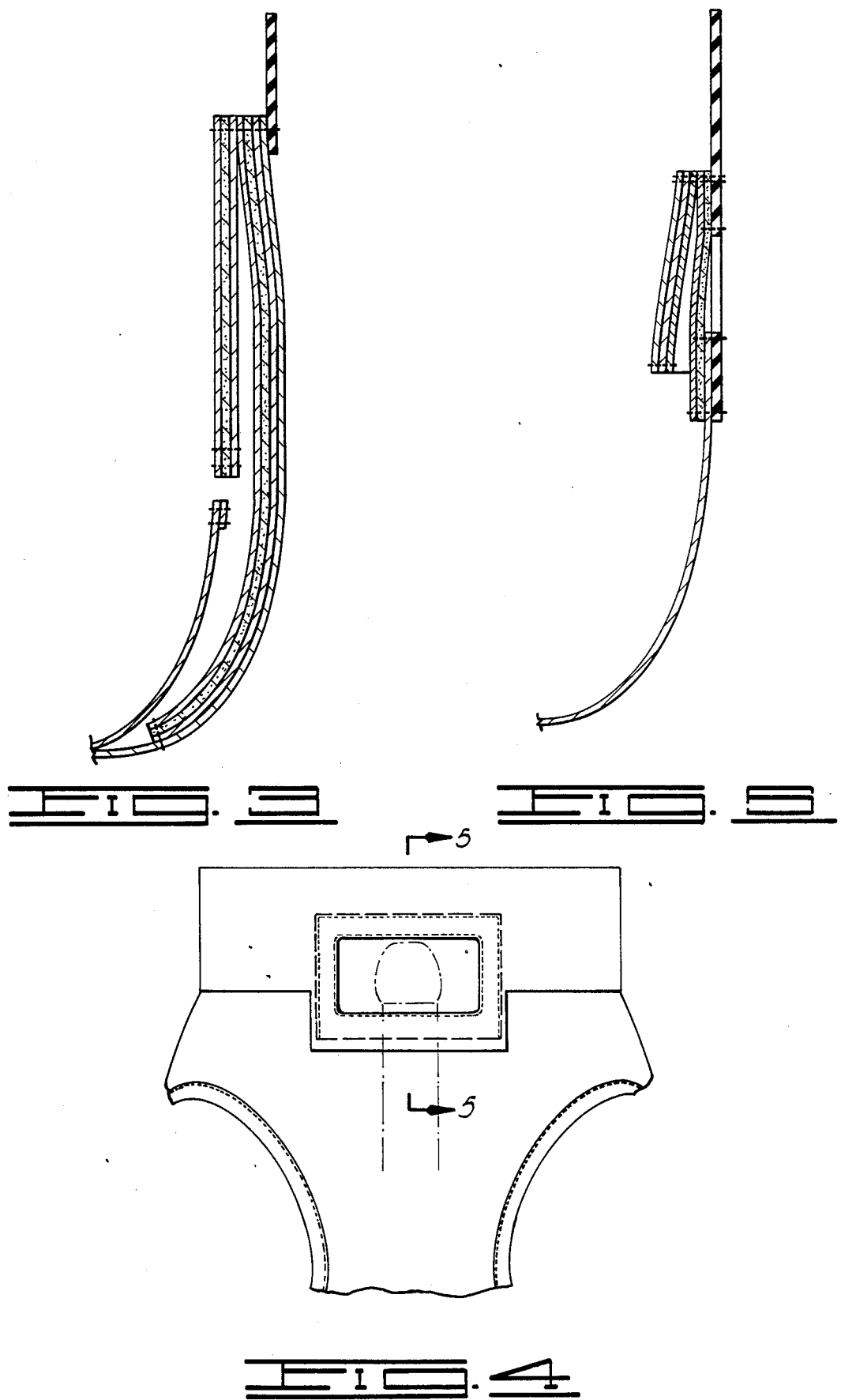
FIG. 3 is a section taken along lines 3—3 of FIG. 2 showing the interior enclosure.
FIG. 4 is a front view of an alternative sports design of the men's briefs with interior parts shown in phantom.
FIG. 5 is a vertical section taken along lines 5—5 of FIG. 4 showing the internal enclosure structure.

FIG. 3 illustrates in sectional view the essential components of containment structure 24. Thus, as the rear panel 18 extends around through crotch panel 20 (FIG. 1), either continuously or by stitched sections, the panel is continued upward to include the cosmetic panel 22. An inner panel 40 of SPANDEX TM material extends from the front portion of waist band 12 downward and around through the crotch to be secured as at stitches 42 (FIG. 1). All plies of containment structure 24 are stitched at the forward bottom of waistband 12 by a seam stitch 44.

Immediately behind cosmetic panel 22 there are positioned respective plies of outer front panel 46, padding panel 48 and outer contact panel 50, and these panels are secured at top and bottom by stitch 44 and a stitch 52, respectively. The outer front panel 46 is preferably formed from such as Lycra SPANDEX TM, a thin, two-way stretch light fabric, and the padding panel 48 is formed from a thicker material, e.g. a ⅛ inch polyester batting material of very light weight. The outer contact panel 50 is then formed of charmeuse fabric having satin and matte sides and being positioned with the satin side 54 adjacent the interior pocket or enclosure 56 for contact with the penis. It is important that the charmeuse fabric be cut so that the grain lies vertically in the operational attitude, i.e., when worn, thereby to assure maximum satin smoothness.

The rear wall of containment structure 24 is then formed from inner panel 40, a rear padding panel 58 and a rear contact panel 60 as positioned and secured by waist band stitch 44 and a lower stitch 62, as placed across the upper edge of slit 36. Slit 36 extends across the structure 24. The inner panel 40 may be formed of Lycra SPANDEX TM or the like and extended around to be secured by stitch 42 across the seat in rear panel 18 (see FIG. 1). The polyester batting of selected thickness may be used for padding panel 58 as the charmeuse fabric is used for contact panel 60 with a satin side 64 facing into enclosure 56. SPANDEX TM panels 40 and 46 may be overlapping extensions of the body fabric.

In operation, the user dons the briefs by inserting the erected penis through slot 36 for upward disposition within space 4, this constituting the normal or regular type of wearing attitude. The light elastic front panel 46 of SPANDEX TM or the like employs a two-way elastic pressure inwardly against the penis to maintain the member in low profile while the charmeuse contact panels 50 and 60 envelope the penis with the satin finish sides 54 and 64 thereby to provide abrasion free contact. The padding panels 48 and 58 then further contribute to the comfort by their lightweight resilient consistency. The overall effect is one of comfort in all normal activities while greatly lessening the likelihood of any unwanted bulging to the wearer's outer clothes.

FIGS. 4 and 5 illustrate an alternative form of brief 70 which may be termed the sports model since it is designed with greater elasticity to sustain more rugged activity. Thus, a reinforced or heavier waistband 72 is formed of a heavier weight elastic banding as it is attached to the lower underwear paneling 74. The paneling 74 may be constructed unitarily or in sections similar to that shown for brief 10 in FIG. 1, and it may be constructed of SPANDEX TM or cotton ribbed fabric in conventional manner.

The elastic waistband 72 is formed with a rectangular window 76 (see also FIG. 5) behind which is stitched a rectangular panel of a batting 78, e.g., a hammered polyester soft fabric. This panel 78 is then backed by a soft contact panel 80 of charmeuse or the like having satin finish surface 82 facing towards enclosure 84. Panels 78 and 80 are secured behind the panel 76 in waistband 72 by means of a window stitches 86 and 88.

The outer rectangular stitching 86 also retains the inner enclosure wall consisting of a lightweight inner panel 90 of such as SPANDEX TM, inner padding panel 92 of the ⅛ inch polyester batting, and the soft contact panel 94 of charmeuse with satin finish side 96 facing enclosure 84. Panels 90, 92 and 94 are suitably secured by inward seamed stitching 98, and the top portion is secured by outer concentric stitching 88.

In operation, the wearer dons the underwear in similar manner fitting the penis 34 upward within the enclosure 84 so that the head and glans of penis 34 are disposed adjacent window 76. Thus, while there is a tight banding effect around the waist as exerted by the relatively heavy elastic waistband 72, the most sensitive portions of the penis are retained beneath a much softer window portion 76 with lessening of pressure and attendant comfort at all times. Thus, during running or even activity embodying more strenuous and violent movements, the brief 70 is capable of maintaining the erected penis in a safe, comfortable and relatively hidden position for extended periods of activity.

The foregoing discloses a novel form of underwear brief that is particularly adapted for the man having a penile implant of the type which renders the penis permanently rigid. The briefs of the present invention accomplish maximum comfort and safety for the situation while still lessening by a great amount any noticability of the wearer's condition from a view of his outer clothes. The sum of the advantages contributes not only to the wearer's comfort but to his assurance of bearing and relaxation in public activities.

Changes may be made in combination and arrangement of elements as heretofore set forth in the specification and shown in the drawings; it being understood that changes may be made in the embodiments disclosed without departing from the spirit and scope of the invention as defined in the following claims.

What is claimed is:

1. Special purpose underwear briefs for accommodating a prosthetic semi-rigid penis, comprising:
   a waistband of selected elastic material;
   a body coverage part formed of selected light weight fabric material having rear and side panels and including leg holes;
   a front plural ply retaining section included within said
      body coverage part and adapted to fit over said penis which consists of;
      an outer front panel of elastic fabric material sewn to the front of the waistband and extending to the crotch area,
      a padding panel of relatively thick fabric batting material sewn to overlay said outer front panel
      an outer contact panel of soft fabric sewn to overlay said padding panel to present a smooth surface adjacent an enclosure space which receives the penis in an upright position.
      a rear contact panel of soft fabric sewn to said outer contact panel to present a smooth surface to said envelope while defining the back portion of the envelope, a rear padding panel of relative thick fabric batting material sewn to overlay said rear contact panel, and an inner panel of soft fabric material sewn to overlay the rear padding panel.

2. Special purpose underwear briefs as set forth in claim 1 which are further characterized in that:

said inner panel extends down to the crotch area for joinder with the outer front panel and the rear panel of the body coverage part; and a slit is formed horizontally across said inner panel to receive the penis for positioning within said enclosure.

3. Special purpose underwear briefs as set forth in claim 1 wherein:

each of said outer contact panel and said rear contact panel are charmeuse material having a satin finish surface that faces said enclosure.

4. Special purpose underwear briefs as set forth in claim 1 which are further characterized in that:

said outer front panel is formed of two-way stretch elastic fabric of selected weight.

5. Special purpose underwear briefs as set forth in claim 3 which are further characterized in that:

said outer front panel is formed of two-way stretch elastic fabric of selected weight.

6. Special purpose underwear briefs as set forth in claim 5 which are further characterized in that:

said inner panel extends down to the crotch area for joinder with the outer front panel and the rear panel of the body coverage part; and a slit is formed horizontally across said inner panel to receive the penis for positioning within said enclosure.

7. Special purpose underwear briefs as set forth in claim 5 wherein:

said charmeuse material is cut with the grain to lay vertically in the operational attitude of the briefs.

* * * * *